United States Patent [19]
Abe et al.

[11] Patent Number: 5,956,123
[45] Date of Patent: Sep. 21, 1999

[54] APPARATUS FOR OBSERVING CORNEA FOR TRANSPLANTATION

[75] Inventors: Kuniomi Abe; Toru Fujii, both of Nishinomiya, Japan

[73] Assignee: Konan Inc, Nishinomiya, Japan

[21] Appl. No.: 09/113,351

[22] Filed: Jul. 10, 1998

[30] Foreign Application Priority Data

Jul. 10, 1997 [JP] Japan ..................................... 9-184672
Dec. 25, 1997 [JP] Japan ..................................... 9-356433

[51] Int. Cl.⁶ ....................................................... A61B 3/10
[52] U.S. Cl. ........................................................... 351/216
[58] Field of Search ..................................... 351/205, 206, 351/216, 217, 218, 245, 246, 247; 623/5, 6, 4; 435/284.1, 304.1

[56] References Cited

U.S. PATENT DOCUMENTS

| | | |
|---|---|---|
| 4,209,225 | 6/1980 | Abe et al. . |
| 4,370,033 | 1/1983 | Kani et al. . |
| 5,030,575 | 7/1991 | Stofac .................................. 435/284.1 |
| 5,471,261 | 11/1995 | Yoshizo et al. . |
| 5,489,300 | 2/1996 | Capecchi et al. ............................ 623/5 |
| 5,548,354 | 8/1996 | Kasahara et al. . |
| 5,557,351 | 9/1996 | Kasahara et al. . |
| 5,789,240 | 8/1998 | Adulrazik ............................... 435/284.1 |

FOREIGN PATENT DOCUMENTS

| | | |
|---|---|---|
| 9-184672 | of 0000 | Japan . |
| 9-356433 | of 0000 | Japan . |
| 6-327635 | 11/1994 | Japan . |
| 8-071043 | 3/1996 | Japan . |
| 8-206080 | 8/1996 | Japan . |
| 9-056681 | 3/1997 | Japan . |
| 9-094228 | 4/1997 | Japan . |
| 9-094229 | 4/1997 | Japan . |
| 9-313442 | 12/1997 | Japan . |
| 10-057318 | 3/1998 | Japan . |
| 10-127583 | 5/1998 | Japan . |

*Primary Examiner*—George Manuel
*Attorney, Agent, or Firm*—Pillsbury Madison & Sutro LLP

[57] ABSTRACT

An apparatus for observing cornea for transplantation comprising, a transparent receptacle with a transparent window showing excellent flatness, which is able to receive a cornea container (a sample vial), and to pour liquid (water) into said transparent receptacle, a holder holding said transparent receptacle, a supporting table receiving said holder freely rotatebly, and an optical system such as a specular microscope. In place of a cornea container, a cornea exclusive container may be used. Said cornea exclusive container is installed directly in said holder. Optical positioning means such as a mirror(s) and a camera(s) is set up in order to position easily the observing portion by microscope through the transparent window of said transparent receptacle or of cornea exclusive container.

10 Claims, 6 Drawing Sheets

APPARATUS FOR OBSERVING CORNEA FOR TRANSPLANTATION

BACKGROUND OF THE INVENTION

1. Field of the Invention

This invention relates to an apparatus for observing cornea for transplantation, wherein the cornea contained in a cornea container, so-called sample vial, filled with chemical liquid, can be observed, photographically taken and measured as it is through the bottom of the container by means of an optical system such as a specular microscope.

Further, this invention relates to an apparatus for observing cornea for transplantation, wherein the cornea can be exactly observed with easy positioning of transparent receptacle by such optical positioning means as a mirror(s) and a camera(s).

2. Description of the Prior Art

The prior art of technology is to take out cornea contained in a sample vial filled with chemical liquid from the vial and to transfer it into a cornea exclusive container to be positioned in the optical axis of microscope in order to observe, photographically to take and to measure the thickness of the cornea for transplantation and the dimensions and states of cells. This transfer is due to the difficulties of observation of cornea contained in the sample vial as it is by a microscope. That is, said sample vial is originally aimed at the safe transportation and preservation of cornea, and the vial has different dimensions respectively. The vial is also not fabricated for observing through its bottom, the thickness of which is irregular, and its flatness is not constant.

On the contrary a cornea exclusive container has good flatness of surface of the container and can hold the cornea in the center of the container filled with chemical liquid stably by taking out it from a sample vial, as well as exclude air bubbles from the container while putting on the lid and exactly observe through the transparent window of said container by a specular microscope.

However, in order to transfer only cornea from the sample vial to the cornea exclusive container, as mentioned above, to observe, to photograph and to measure, such procedures as opening the lid of vial, taking out cornea, transferring it to an exclusive container and adjusting it into appropriate position, are necessary. And then the problems, that the cornea may be meanwhile damaged and contaminated and the procedure is taking much time, were observed.

OBJECTS OF THE INVENTION

An object of this invention is to provide an apparatus for observing cornea for transplantation, which can dissolve above-mentioned difficulties, receive a cornea container, so-called sample vial, into a transparent receptacle, observe, photographically take and measure through the bottom of transparent receptacle with an optical system such as a specular microscope.

Further object of this invention is to provide an apparatus for observing cornea for transplantation, which can reduce the probable difference and scattering in the flatness of the bottom of sample vial and is able to observe, photograph and measure the exact states of corneal endothelium and epithelium, thickness of cornea and the like through the bottom of transparent receptacle by a specular microscope.

Another object is to provide an apparatus for observing cornea for transplantation, which can observe the cornea in a sample vial accurately, by easy positioning for observation through a transparent window of the transparent receptacle before microscopic observation.

Other object of this invention is to provide an apparatus for observing cornea for transplantation, which can also observe, photograph take and measure using a cornea exclusive container holding the cornea.

DETAILED DESCRIPTION OF THE PREFERRED EMBODIMENTS

Figure 1:
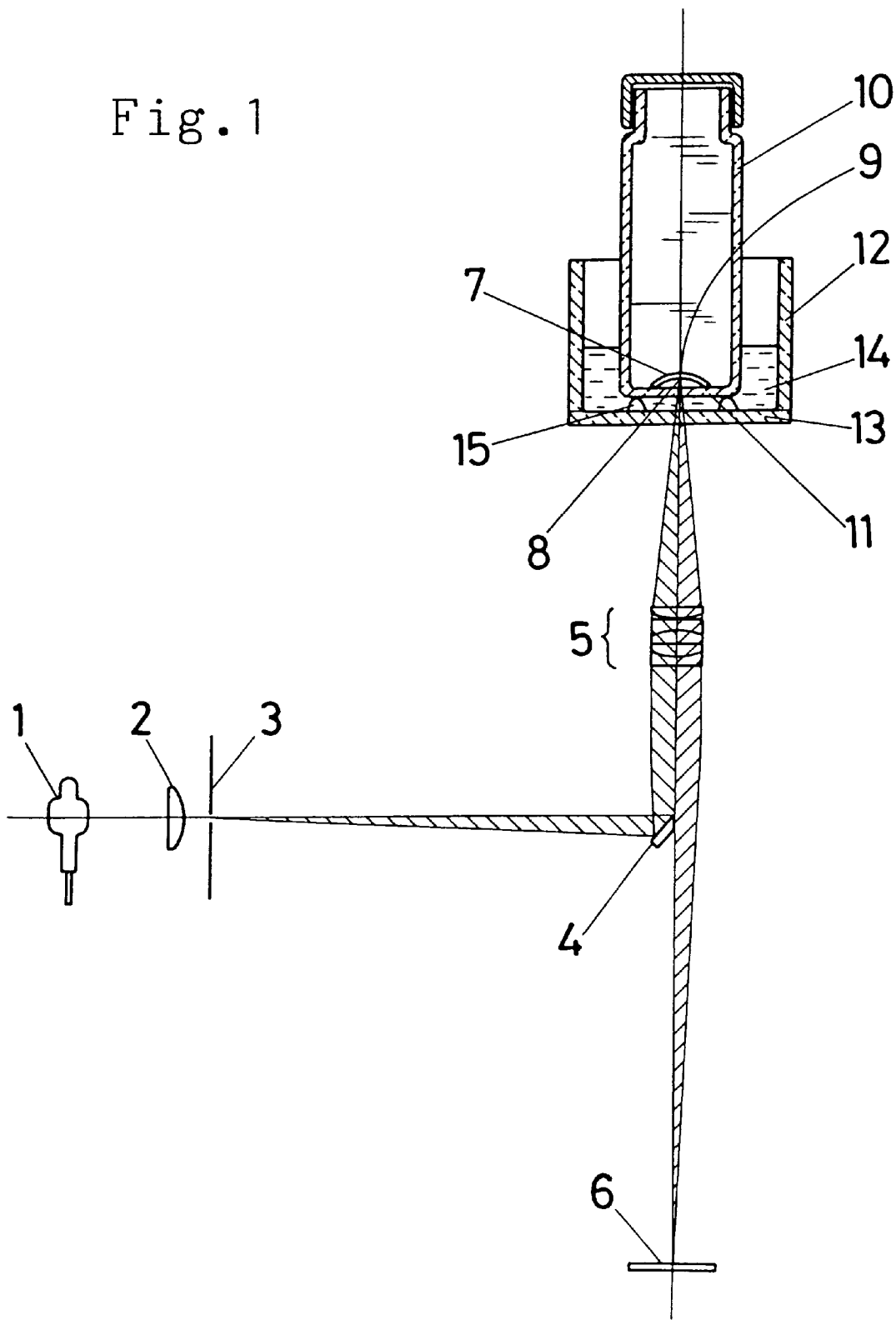
FIG. 1 shows an optical observing system for cornea contained in a cornea container filled with chemical liquid.

An optical system to be used for this invention will be explained by FIG. 1. 1 is a light source such as illumination lamp. 2 is condenser lens. 3 is a lighting slit. From light source 1 corneal endothelium 8 in cornea 7 is lit up through a lighting slit 3 by means of a mirror 4 and objectives 5.

On this occasion, the light beam enters through the left half of objectives 5 in oblique direction. The slant lighting let the slit-reflecting image of corneal endothelium go through the right half of objectives 5 as shown in figure and focus on, for example, CCD camera 6. The above-mentioned signs from 1 to 6 constitute a specular microscope.

Figure 2:
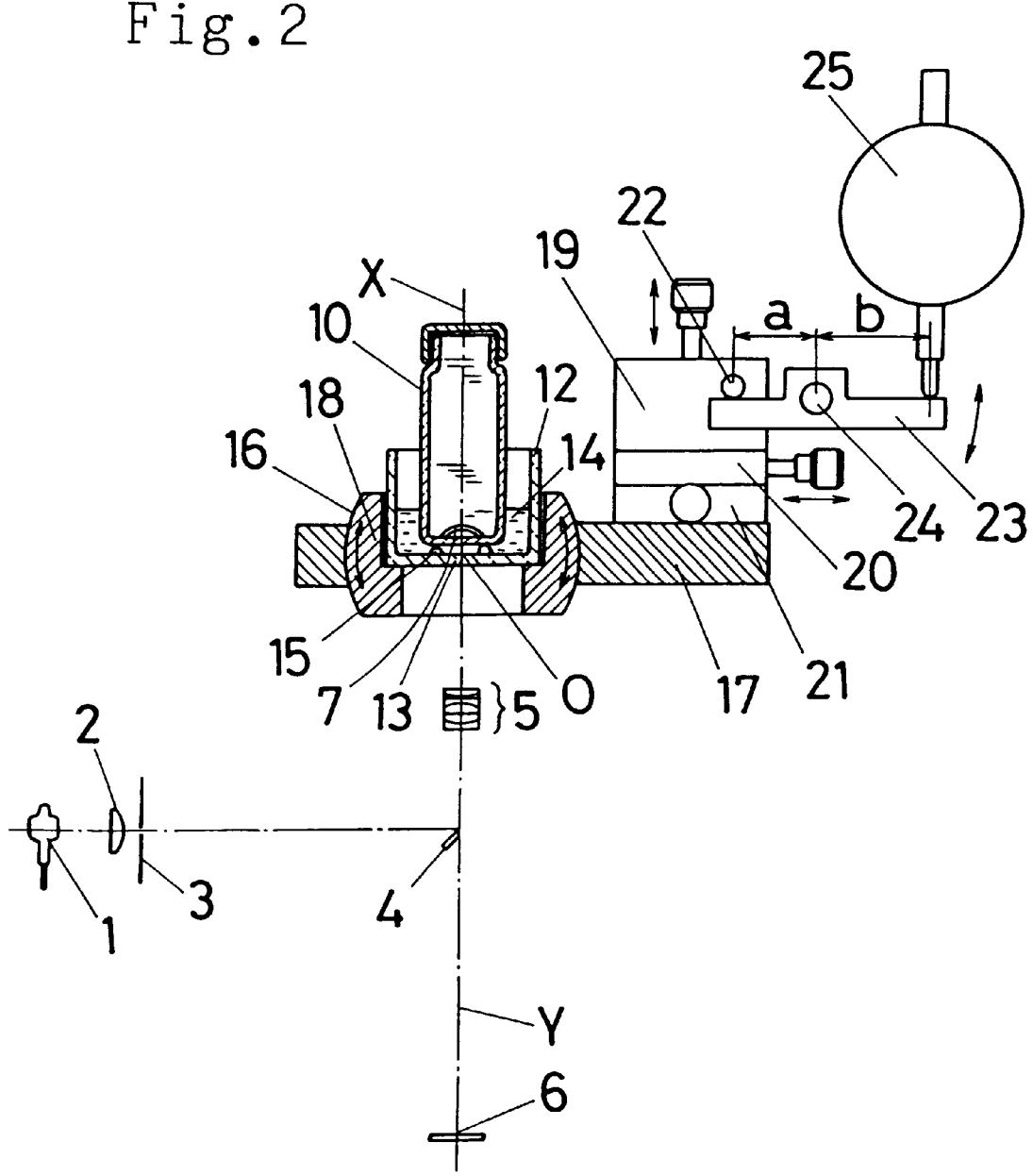
FIG. 2 is a cross-sectional view of observing mechanism for cornea.

The construction of this invention will be further explained in detail with the mechanism shown on FIG. 2.

Cornea 7 is contained in a cornea container (a sample vial) 10 filled with chemical liquid. 11 is the bottom of the cornea container 10. 12 is a transparent receptacle into which water may be poured, and which is able to receive a cornea container 10. 13 is a transparent window of the transparent receptacle. 14 is water which is poured into the transparent receptacle 12 and forms a water layer between the bottom of the sample vial 10 and the transparent window 13 of the transparent receptacle 12.

15 is a spacer, which prevents the direct contact of the bottom 11 of the cornea container 10 with the transparent window 13 and let water flow through in order to drive out air bubbles especially at a gap while pouring water into the transparent receptacle 12.

16 is a joint portion of the holder for spherical movement, where holder 18 is set up in a supporting table 17 in freely rotatebly. Holder 18 has a vertical opening passing through downward and stoppers at the inside of the opening. Then the holder can be set up a transparent receptacle 12 at the upper portion of the opening and has an open space at the lower portion through which observation is carried out by an optical system.

As a joint portion for spherical movement 16, besides a convex or concave sphere type joint as shown on figure, free-rotational mechanism with fulcrums of double orthogonal axes may be applied, but it is not limited to this.

In order to observe corneal endothelium 8 in cornea 7 the holder 18 holding the transparent receptacle 12 along with the joint portion for spherical movement 16 may be moved and adjusted by means of adjusting mechanisms 19, 20 and 21 attached to the supporting table 17 until the slit reflecting image of corneal endothelium will focus on CCD camera 6. 19 is a vertical (Y axis) adjusting mechanism, 20 is a horizontal (X axis) adjusting mechanism and 21 is a transversal (Z axis) adjusting mechanism, respectively.

The distance between both focussing positions of corneal endothelium and epithelium surfaces (travelling distance of supporting table) is the corneal thickness. The vertical adjusting mechanism 19 which can be moved the supporting table 17 in vertical direction, is equipped with a lever-contacting rod 22, and which moves the transparent receptacle 12 on the holder 18 and the sample vial 10 received in the transparent receptacle 12 together in vertical direction by means of supporting table 17.

A lever 23, whose one en d contacts the rod 22 and whose another end contacts an indicator 25, is maintained by an axis 24 at the point for the ratio of the lengths relating to the refractive indexes of air and cornea, respectively (a:b= 1:1.376), and thus the moving quantity, that is the distance between both focussing positions of corneal endothelium and epithelium surfaces, can be read as the corneal thickness by the indicator 25.

Therefore, only reading the indicator is sufficient, and the proportional calculation of refractive indexes as before became unnecessary. As indicator 25 such apparatus which is able to indicate variation mechanically and electrically as a dial gauge as shown on figure, magnetic scale and the like, can be applied.

As the transparent receptacle 12 with a transparent window showing excellent flatness, being able to contain a cornea container and to pour liquid (water), is mounted on the holder 18, the distortion of refractive index due to the unevenness of the bottom of sample vial 10 can be reduced as the difference of refractive indexes between the water in the transparent receptacle 12 and the bottom 11 of the sample vial 10 can be diminished in spite of the irregular thickness of the bottom 11 of the cornea container 10, and hence the focussing ability on camera can be improved.

An optical system, in which the light from an illumination lamp 1 by means of mirror 4 and the left half of objective lens 5 passes through the transparent window 13 of the transparent receptacle 12, the gap filled with water 14 and the bottom 11 of the sample vial 10, lightens the cornea 7 in the sample vial 10 through the lighting slit 3, and the reflected light can be focussed on CCD camera 6 by means of the right half of said objective lens 5, enabled us accurately to observe, to take photograph and to measure.

The transparent receptacle 12 may be preferably a transparent glass vessel, but it does not be limited to this. The holder holding a transparent receptacle can be moved vertically, horizontally and transversally by means of each adjusting mechanism as well as rotated by a holder around a fulcrum (O) of the center of curvature in cornea in order to coincide the optical axis (X) of cornea with the optical axis (Y) of the optical system, and hence the setting of the observing site of cornea is facilitated. As a vertical, horizontal or transversal adjusting mechanism a mechanism sliding the surface mutually to be slid by means of a screw and the like, may be used, but not limited to this.

In place of a sample vial as a cornea container, an exclusive cornea container holding the cornea can be applied for observing by installed directly in a holder 18.

Figure 3:
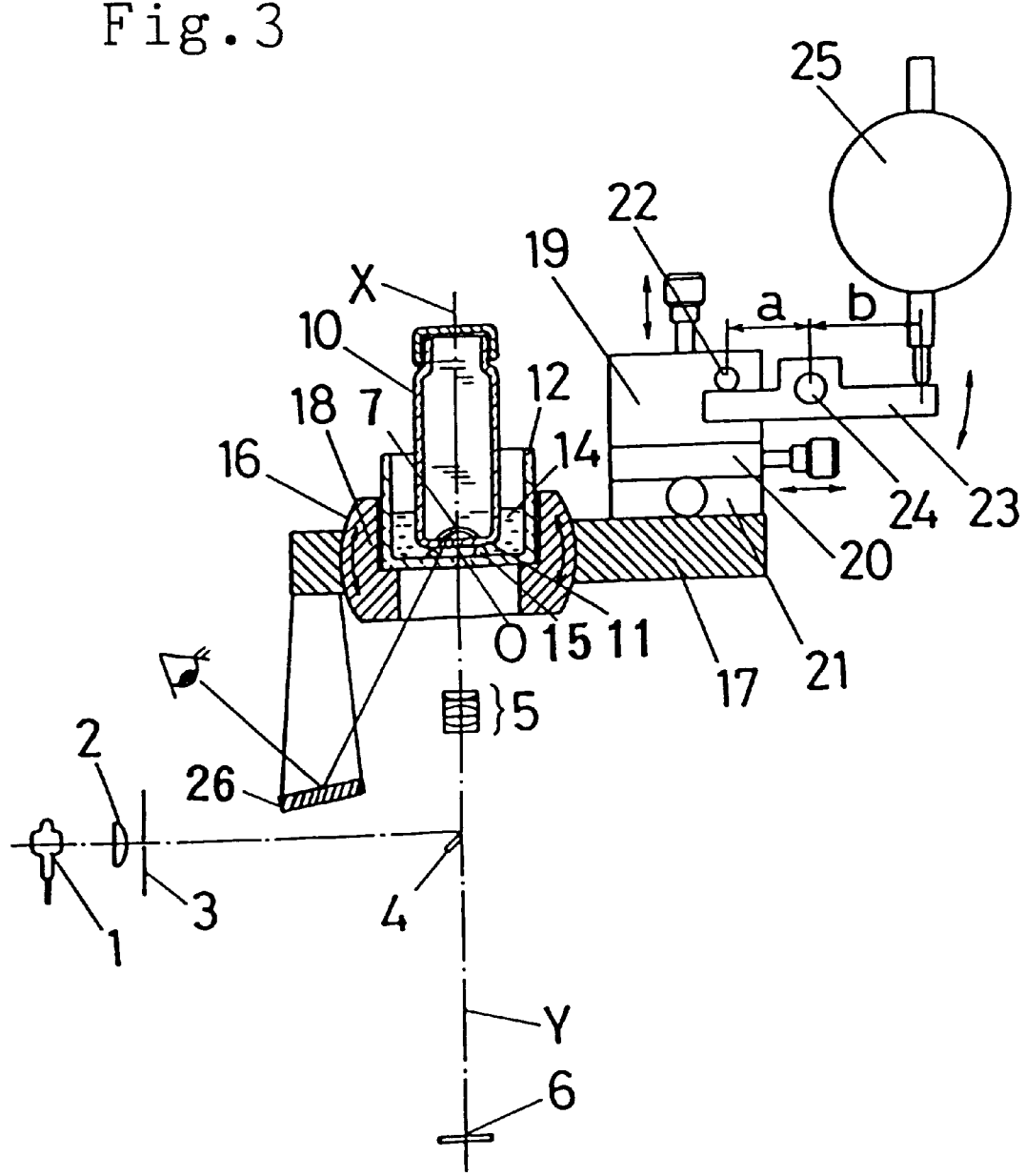
FIG. 3 is a cross-sectional view of observing mechanism for cornea with an optical positioning means.

FIG. 3 shows a positioning means 26 using a mirror, which is fixed to a supporting table 17 as one body, and the observing site in the optical system can be seen through a sample vial 10 from the transparent window of transparent receptacle 12 from the lower side of the holder 18, and hence the control of coinciding the position of cornea in the transparent receptacle with the optical system 1–6 becomes to be more easily performed.

That is, as the light beam from an illumination lamp 1 can be observed as a small light-spot in the bottom of the transparent receptacle, it can be utilized as a reference. Besides, any device, enabling the observing site to be looked, may be applied, for example, small TV camera.

Figure 4:
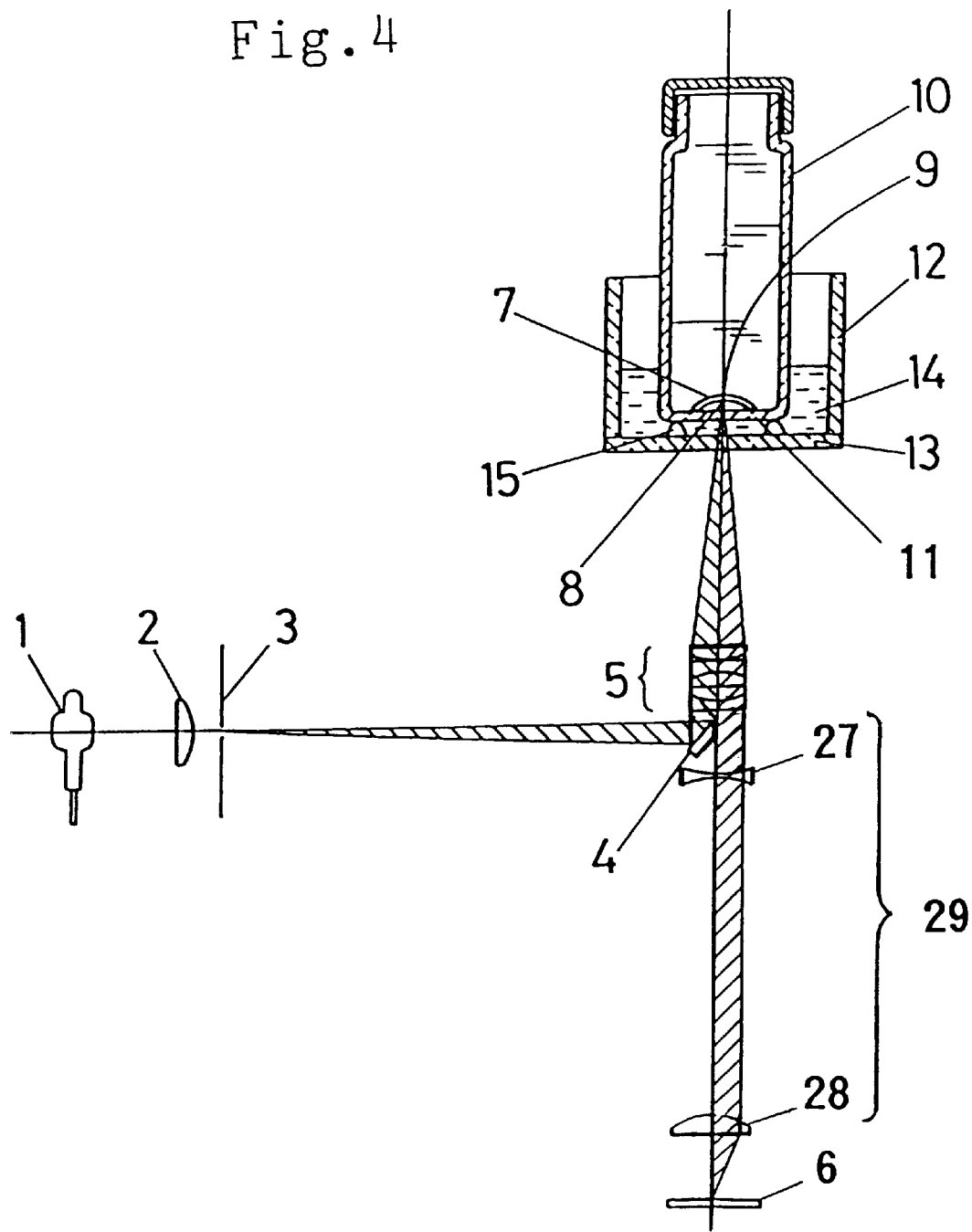
FIG. 4 is a cross-sectional view of observing mechanism for cornea with another optical positioning means.

FIG. 4 is an example, where a positioning means consisting of a low-magnifying lens 27 and low-magnifying lens (focussing lens) 28 is equipped and the position of the holder is determined by CCD camera. Lenses 27 and 28 as a set are inserted from side into the optical system of microscope, taken out at the step of finishing location of the holder, and thus only some focussing adjustment becomes sufficient for observing cornea. 29 shows a low-magnifying lens unit for light positioning. In this example the low-magnifying and wide-angle positioning optical system enables the observing site to be looked wider and the adjustment becomes more easier.

The peeping at the observing site in the transparent receptacle 12 from its transparent window by a positioning means 26 with mirror 26, optical system 27, 28, 29 and the like, makes it facilitated to locate the holder 18 accurately, even if the peeping from above of the sample vial is impossible because of turbidity in the lid of sample vial 10 or the cornea 7 does not lie in the proper position because of its movement within the chemical liquid.

In this invention a transparent receptacle 12 having the excellent flatness of its transparent window 13 is used, which is able to receive a cornea container 10 (a sample vial) as it is, and enables to pour the liquid (water) into the transparent receptacle. Thus, while observing through the transparent window of the transparent receptacle with a microscope, the distortion in optical refraction due to the dispersion of flatness of the cornea container 10 can be reduced by passing through water layer 14 forming and filling the gap between the bottom 11 of cornea container and the transparent window 13 of transparent receptacle.

A spacer 15 is set up between the transparent window 13 of the transparent receptacle and the bottom 11 of the cornea container, and when water is filled in the transparent receptacle, water layer is surely formed at the transparent window of the transparent receptacle so as to remove air bubbles.

As holder 18 is maintained free-rotationally on supporting table 17, the transparent receptacle 12 can be freely rotated by means of the holder 18, the center (0) of curvature in cornea 7 can be easily adjusted in accordance with the optical axis Y, and hence the observation with the specular microscope 1–6 becomes facilitated while observing corneal endothelium 8 and epithelium 9. When changing the observing part of cornea by rotating of said holder, the transitional adjustment in any direction such as vertical, horizontal and transversal can be minimized.

Supporting table 17 is equipped with an adjusting mechanism enabling the optical axis (X) of cornea in a cornea container to be coincide with the optical axis (Y) of the specular microscope, and thus the transitional adjustment for observation became easily feasible.

A vertical adjusting mechanism 19 is provided with an indicator 25 for the moving quantity in accordance with refractive index of cornea, and hence the corneal thickness can be directly observed by visual inspection without proportional calculation due to the difference of refractive indices between air and cornea.

As the positioning means such optical systems as mirror, camera and the like were furnished, the observing site from the transparent window of transparent receptacle 12 by a microscope can be peeped into upwards from downside, and the positional adjustment became facilitated by operating the holder 18 of sample vial 10 utilizing the spot lit with the observing light as a reference.

Figure 5:
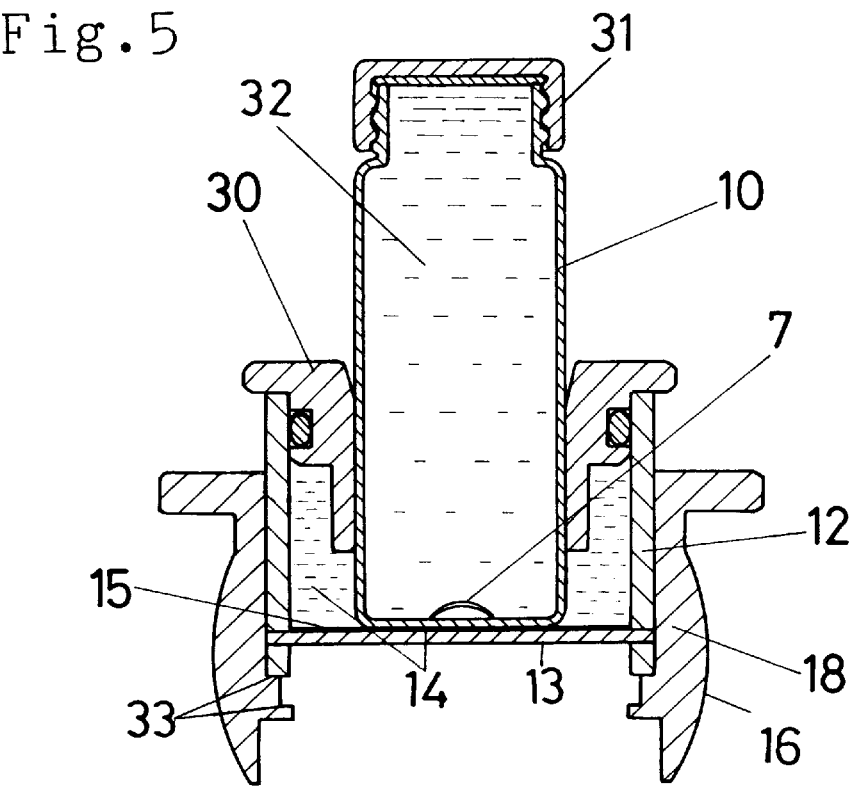
FIG. 5 is an enlarged cross-sectional view of a cornea container.

FIG. 5 shows an enlarged cross-sectional view of the cornea container 10 installed in the holder 18 using a sub-supporter 30. 31 is a lid of the container. 32 is a chemical liquid filled up the container. 33 are stoppers made up at the inside of the opening. The cornea container is held on the first stopper 33.

As shown in the above mentioned explanation the setting of a cornea container 10 in a transparent receptacle 18 makes it possible to observe the thickness, dimensions and the state of cornea 7 from the transparent window 13 of the transparent receptacle 12 as it is by optical system such as a microscope, and hence the easy and rapid observating, photographing or measuring is feasible.

Even if the bottom surface of the cornea container be irregular, the spacer 15 under the bottom enables water to be flow through and the water layer is formed by being filled up the gap, and thus obtained reducing of the distortion in refractive index made it easier to observe from the bottom of the cornea container.

Besides, the free rotation of the transparent receptacle by means of joint portion 16 through a holder on a supporting table 17 makes it very easy to adjust the orientation of the center of corneal curvature and the optical axis of microscope.

Further, as vertical, horizontal and transversal adjusting mechanisms 19, 20 and 21 are equipped on the supporting table 17, the easy coinciding of both optical axes in cornea in the cornea container and the optical system makes it possible to adjust position accurately.

And also as the indicator, which can confirm the displacement in the vertical adjusting mechanism by converting the difference of refractive indexes between air and cornea automatically, is equipped, the displacement between the focussing positions of corneal endothelium and corneal epithelium can be read as corneal thickness automatically.

Also, the use of such optical positioning means as mirror and the like, enables the locating of the observing site in the transparent window of the transparent receptacle easily to be carried out through the holder.

In place of a cornea container 10, it may be used an exclusive cornea container holding the cornea as it is by mounting it in the holder 18 directly. The state of cornea contained in said exclusive cornea container can be observed, photographed or measured through the transparent window (lid) in the same way as mentioned above.

Figure 6:
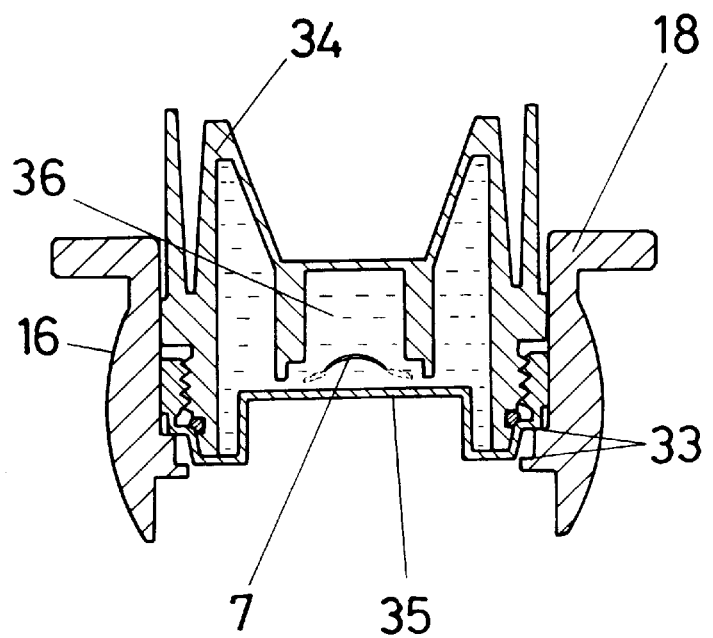
FIG. 6 is a cross-sectional view of a cornea exclusive container installed in a holder.

FIG. 6 shows an exclusive cornea container 34 which is installed in the upper portion of the holder 18 turning the container upside down. The container 34 is held on the first stopper 33. 35 is a lid (transparent window) through which observation can be carried out. 36 is a chemical liquid filled up the container 34.

Figure 7:
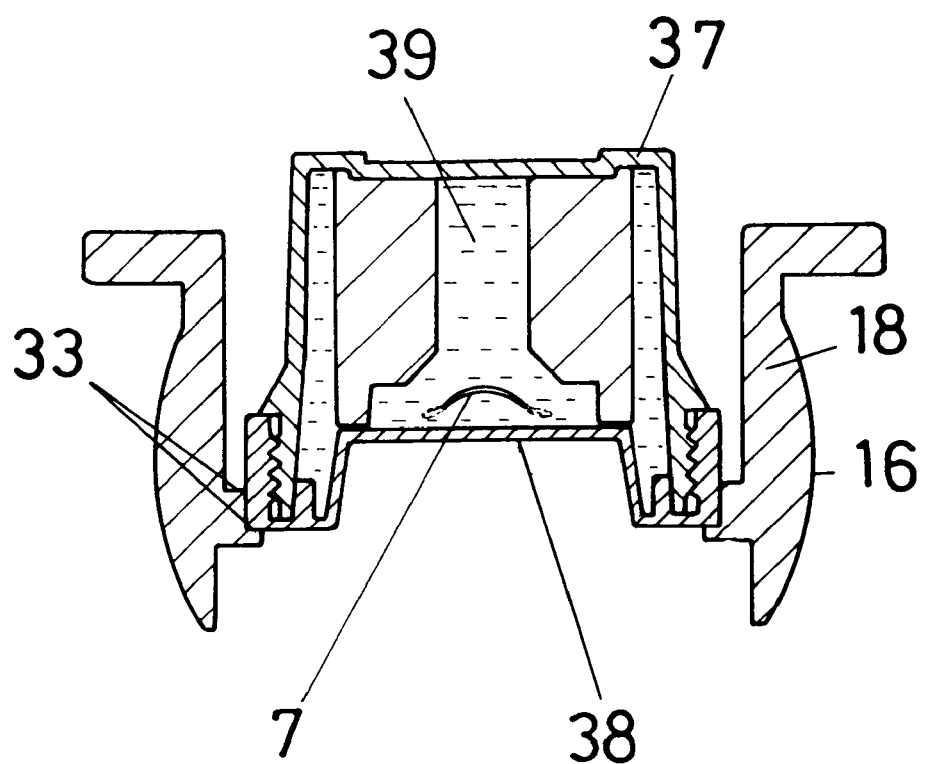
FIG. 7 is a cross-sectional view of another type of cornea exclusive container installed in a holder.

FIG. 7 shows another type of the exclusive cornea container 37 installed in the upper portion of the holder 18 turning the container upside down. 38 is a lid (transparent window) through which observation can be carried out. 39 is a chemical liquid filled up the container 37. The container 37 is held on the second stopper 33.

The type of the containers 10, 34 and 37 mentioned in FIG. 5, FIG. 6 and FIG. 7 is respectively different. However each container has been designed so that the cornea contained in the container filled with chemical liquid is held at the respectively equal position. Therefore any container may be used and installed in the holder as it is and all types of container may be alternated easily.

Moreover, as the cornea is positioned near the center of rotation of the holder, it is easy to adjust the position of holder and is sufficient to adjust slightly.

As mentioned above, measuring of thickness and dimensions of the cornea and observing the state of the cornea are carried out quite easily in case of the cornea container is installed in the holder through transparent container and the exclusive cornea container is installed in the holder as well, by means of optical system and positioning means.

What is claimed is:

1. An apparatus for observing cornea for transplantation comprising:
    (1) a transparent receptacle with a transparent window showing excellent flatness, which is able to receive a cornea container, and to pour liquid (water) into said transparent receptacle,
    (2) a holder holding said transparent receptacle,
    (3) a supporting table receiving said holder freely rotatably, and
    (4) an optical system such as a specular microscope.

2. An apparatus for observing cornea for transplantation according to claim 1 wherein a spacer is set up at the bottom of said transparent receptacle in order to enable the liquid filled up the gap and form a water layer between the transparent window of said transparent receptacle and the bottom of said cornea container.

3. An apparatus for observing cornea for transplantation according to claim 1 wherein a holder is set so as to rotate around the center of curvature (O) of the cornea in said cornea container.

4. An apparatus for observing cornea for transplantation according to claim 1 wherein an adjusting mechanism is equipped for enabling said supporting table to move three-dimensionally in order nearly to coincide the optical axis (X) of the cornea in said cornea container with the optical axis (Y) of said specular microscope.

5. An apparatus for observing cornea for transplantation according to claim 1 wherein an indicator is installed in the supporting table, by which the vertical adjusting mechanism indicates displacement according to the refractive index of cornea.

6. An apparatus for observing cornea for transplantation according to claim 1 wherein the thickness, dimensions and states of the cornea can be observed, photographically taken or measured optically through the transparent window of the transparent receptacle, water and the bottom of the cornea container by a specular microscope.

7. An apparatus for observing cornea for transplantation according to claim 1 wherein a cornea exclusive container holding the cornea is installed in said holder.

8. An apparatus for observing cornea for transplantation according to claim 1 wherein said holder has a vertical opening passing through downward and stoppers to be held the container at the inside of the opening.

9. An apparatus for observing cornea for transplantation comprising:
    (1) a transparent receptacle with a transparent window showing excellent flatness, which is able to receive a cornea container, and to pour liquid into said transparent receptacle,
    (2) a holder holding said transparent receptacle,
    (3) a supporting table receiving said holder freely rotatebly,
    (4) an optical system such as a specular microscope, and
    (5) such optical positioning means as a mirror(s) and a camera(s) in order to position the observing portion by microscope through the transparent window of said transparent receptable.

10. An apparatus for observing cornea for transplantation according to claim 9 wherein a cornea exclusive container holding the cornea is installed in said holder.

* * * * *